US011998908B2

(12) United States Patent
Iwata

(10) Patent No.: US 11,998,908 B2
(45) Date of Patent: Jun. 4, 2024

(54) PREPROCESSING DEVICE, PREPROCESSING METHOD, AND NON-TRANSITORY COMPUTER READABLE MEDIUM STORING PROGRAM

(71) Applicant: Shimadzu Corporation, Kyoto (JP)

(72) Inventor: Hiroshi Iwata, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 179 days.

(21) Appl. No.: 17/721,572

(22) Filed: Apr. 15, 2022

(65) Prior Publication Data

US 2022/0331793 A1 Oct. 20, 2022

(30) Foreign Application Priority Data

Apr. 20, 2021 (JP) ................................. 2021-070866

(51) Int. Cl.
*G01N 33/68* (2006.01)
*B01L 3/00* (2006.01)
*C07C 309/65* (2006.01)
*C07C 309/73* (2006.01)
*G01N 1/40* (2006.01)
(Continued)

(52) U.S. Cl.
CPC ......... *B01L 3/50255* (2013.01); *B01L 3/5635* (2013.01); *G01N 1/4077* (2013.01); *B01L 2200/0647* (2013.01); *B01L 2200/0684* (2013.01); *B01L 2300/0627* (2013.01);
(Continued)

(58) Field of Classification Search
CPC .... G01N 33/6815; G01N 21/33; G01N 21/64; G01N 33/52; G01N 2800/00; G01N 33/6812; C07C 309/65; C07C 309/73; C07C 277/66
See application file for complete search history.

(56) References Cited

U.S. PATENT DOCUMENTS 4,933,092 A 6/1990 Aunet et al.
2004/0185437 A1 9/2004 Hermet et al.
(Continued)

FOREIGN PATENT DOCUMENTS

JP 6-500403 1/1994
JP 10-215859 8/1998
(Continued)

OTHER PUBLICATIONS

Office Action dated Oct. 13, 2023 in related U.S. Appl. No. 17/071,274.
(Continued)

*Primary Examiner* — Jennifer Wecker
*Assistant Examiner* — Oyeleye Alexander Alabi
(74) *Attorney, Agent, or Firm* — Wenderoth, Lind & Ponack, L.L.P.

(57) ABSTRACT

In a recovery device, a removing target such as a blood cell is removed from a liquid sample in a sample container using a first filter unit, and a microorganism is filtered from the liquid sample using a second filter unit. A controller causes a first switch to block a flow channel in response to a sensor detecting a bubble. A medium flows from a second connection unit of the second filter unit toward a first connection unit. Thus, the microorganism filtered by the second filter unit is recovered by a recovery container together with the medium.

7 Claims, 14 Drawing Sheets

(51) Int. Cl.
    *G01N 21/33*    (2006.01)
    *G01N 21/64*    (2006.01)
    *G01N 33/52*    (2006.01)

(52) U.S. Cl.
    CPC ............... *B01L 2300/0681* (2013.01); *G01N 2001/4088* (2013.01)

(56) References Cited

U.S. PATENT DOCUMENTS

| | | |
|---|---|---|
| 2007/0298451 A1 | 12/2007 | Ribault et al. |
| 2012/0088227 A1 | 4/2012 | Gruebl et al. |
| 2016/0251628 A1* | 9/2016 | Vincent ............... C12N 5/0688 424/93.7 |
| 2017/0191114 A1 | 7/2017 | Kamba et al. |
| 2020/0046891 A1 | 2/2020 | Yamashita et al. |
| 2021/0113968 A1 | 4/2021 | Iwata |
| 2021/0116337 A1 | 4/2021 | Iwata |

FOREIGN PATENT DOCUMENTS

| | | |
|---|---|---|
| JP | 2003-194806 | 7/2003 |
| JP | 2005-503803 | 2/2005 |
| JP | 2006-262891 | 10/2006 |
| JP | 2014-117220 | 6/2014 |
| JP | 2015-216875 | 12/2015 |
| WO | 92/17110 | 10/1992 |
| WO | 2016/194463 | 12/2016 |
| WO | 2018/194061 | 10/2018 |
| WO | 2019/163452 | 8/2019 |

OTHER PUBLICATIONS

Office Action dated Apr. 14, 2023 in related U.S. Appl. No. 17/071,274.
Notice of Reasons for Refusal dated Jul. 25, 2023 in Japanese Patent Application No. 2019-191185, with English language translation.
Office Action dated Oct. 5, 2022 in U.S. Appl. No. 17/069,043.
Office Action dated May 30, 2023 in related U.S. Appl. No. 17/069,043.
Concise Medical Dictionary, 2014, Oxford University Press, 8th edition , definition of 'microorganisrn'.
Fothergill, Amy et al., "Rapid Identification of Bacteria and Yeasts from Positive-Blood-Culture Bottles by Using a Lysis-Filtration Method and Matrix-Assisted Laser Desorption Ionization-Time of Flight Mass Spectrum Analysis With the SARAMIS Database", Journal of Clinical Microbiology, Mar. 2013, vol. 51, No. 3, pp. 805-809.
Christner, Martin et al., "Rapid Identification of Bacteria from Positive Blood Culture Bottles by Use of Matrix-Assisted Laser Desorption-Ionization Time of Flight Mass Spectrometry Fingerprinting", Journal of Clinical Microbiology, May 2010, vol. 48, No. 5, pp. 1584-1591.
Deponte, S. et al., "Biomagnetic separation of *Escherichia coli* by use of anion-exchange beads: measurement and modeling of the kinetics of cell-bead interactions", Analytical and Bioanalytical Chemistry, 2004, vol. 379, pp. 419-426.
Office Action dated Jan. 17, 2023, in U.S. Appl. No. 17/071,274.
Notice of Reasons for Refusal dated Dec. 20, 2022 in Japanese Patent Application No. 2019-191185, with English language translation.
Office Action dated Dec. 20, 2022 in U.S. Appl. No. 17/069,043.
Notice of Reasons for Refusal issued Dec. 26, 2023 in Japanese Patent Application No. 2020-153761 with English-language translation.
Notice of First Examination Opinion issued Jan. 22, 2024 in Chinese Patent Application No. 202011097284.2 with English-language translation.
Decision of Refusal issued Feb. 6, 2024 in Japanese Patent Application No. 2019-191185 with English-language translation.
Advisory Action issued Feb. 5, 2024 in U.S. Appl. No. 17/071,274.

* cited by examiner

PREPROCESSING DEVICE, PREPROCESSING METHOD, AND NON-TRANSITORY COMPUTER READABLE MEDIUM STORING PROGRAM

BACKGROUND OF THE INVENTION

Field of the Invention

The present invention relates to preprocessing of a liquid sample.

Description of the Background Art

Conventionally, various studies have been made on a preprocessing method of a liquid sample. For example, a method for removing a blood cell component hindering measurement, recovering the microorganism, and culturing the recovered microorganism is known in order to identify the microorganism such as a bacterium contained in blood. As an example of the method, there is disclosed a method in which a cell lysate is added to a blood culture solution to dissolve a cell membrane such as a blood cell, the cell membrane is then filtered with a filter, and a substance recovered on the filter is scraped off with a cotton swab to recover the bacterium and the like in the blood culture solution (Amy Fothergill, Vyjayanti Kasinathan, Jay Hyman, John Walsh, Tim Drake, and Yun F. (Wayne) Wang, "Journal of Clinical Microbiology", 51, 805-809 (2013)).

SUMMARY OF THE INVENTION

The above-described method requires a manual operation of scraping the microorganism with the cotton swab, and is not suitable for automation.

The present invention has been made to solve the problem, and an object of the present invention is to provide a technique capable of automating the recovery of the microorganism.

A preprocessing device of the present disclosure includes: a sample container that accommodates a liquid sample containing a blood cell; a first filter unit that includes a first filter for removing the blood cell from the liquid sample in the sample container; and a second filter unit that includes a second filter, a first connection unit, and a second connection unit, the second filter configured to capture a microorganism that can be contained in the liquid sample, and the first connection unit and the second connection unit facing each other with the second filter interposed between the first connection unit and the second connection unit. A bubble point of the second filter is higher than a bubble point of the first filter. A first flow channel, a second flow channel, and a third flow channel are formed in the preprocessing device. The first flow channel connects the second filter unit to the sample container and the first filter unit through the first connection unit, and connects the second filter unit to the waste liquid recovery unit that receives a waste liquid discharged from the second filter unit, through the second connection unit. The second flow channel connects the second filter unit to a cleaning solution accommodation unit that accommodates a cleaning solution for cleaning the second filter, through the first connection unit, and connects the second filter unit to the waste liquid recovery unit through the second connection unit. The third flow channel connects the second filter unit to a recovery solution accommodation unit that accommodates a recovery solution for recovering the microorganism captured by the second filter, through the second connection unit, and connects the second filter unit to a recovery unit that accommodates the recovery solution passing through the second filter unit, through the first connection unit. The preprocessing device of the present disclosure further includes a blocking element that blocks the first flow channel in response to a decrease in a remaining amount of the liquid sample in an upstream position with respect to the second filter unit in the first flow channel.

A pretreatment method of the present disclosure includes removing a removing target from a liquid sample accommodated in a sample container using a first filter and filtering a microorganism from a filtrate of the first filter using a second filter. A bubble point of the second filter is higher than a bubble point of the first filter. The filtering the microorganism including supplying the filtrate of the first filter to one side of the second filter and receiving a waste liquid from an other side of the second filter. The preprocessing method of the present disclosure further includes blocking a flow channel between the second filter and the sample container in response to a decrease in a remaining amount of the liquid sample in an upstream position with respect to the second filter in the filtering the microorganism. The preprocessing method of the present disclosure further includes supplying a cleaning solution to the one side of the second filter and receiving a waste liquid from the other side of the second filter to clean the second filter. The pretreatment method of the present disclosure further includes supplying a recovered liquid to the other side of the second filter and receiving the recovered liquid from the one side of the second filter to recover the microorganism from the second filter.

A non-transitory computer-readable medium storing a program executed by a computer to control a preprocessing device including a first filter and a second filter, the program causing the computer to remove a removing target from a liquid sample accommodated in a sample container using the first filter and filter a microorganism from a filtrate of the first filter using the second filter. A bubble point of the second filter is higher than a bubble point of the first filter. The filtering the microorganism including supplying the filtrate of the first filter to one side of the second filter and receiving a waste liquid from an other side of the second filter. The program further causes the computer to block a flow channel between the second filter and the sample container in response to a decrease in a remaining amount of the liquid sample in an upstream position with respect to the second filter in the filtering the microorganism. The program further causes the computer to supply a cleaning solution to the one side of the second filter and receive a waste liquid from the other side of the second filter to clean the second filter. The program further causes the computer to supply a recovered liquid to the other side of the second filter and receive the recovered liquid from the one side of the second filter to recover the microorganism from the second filter.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
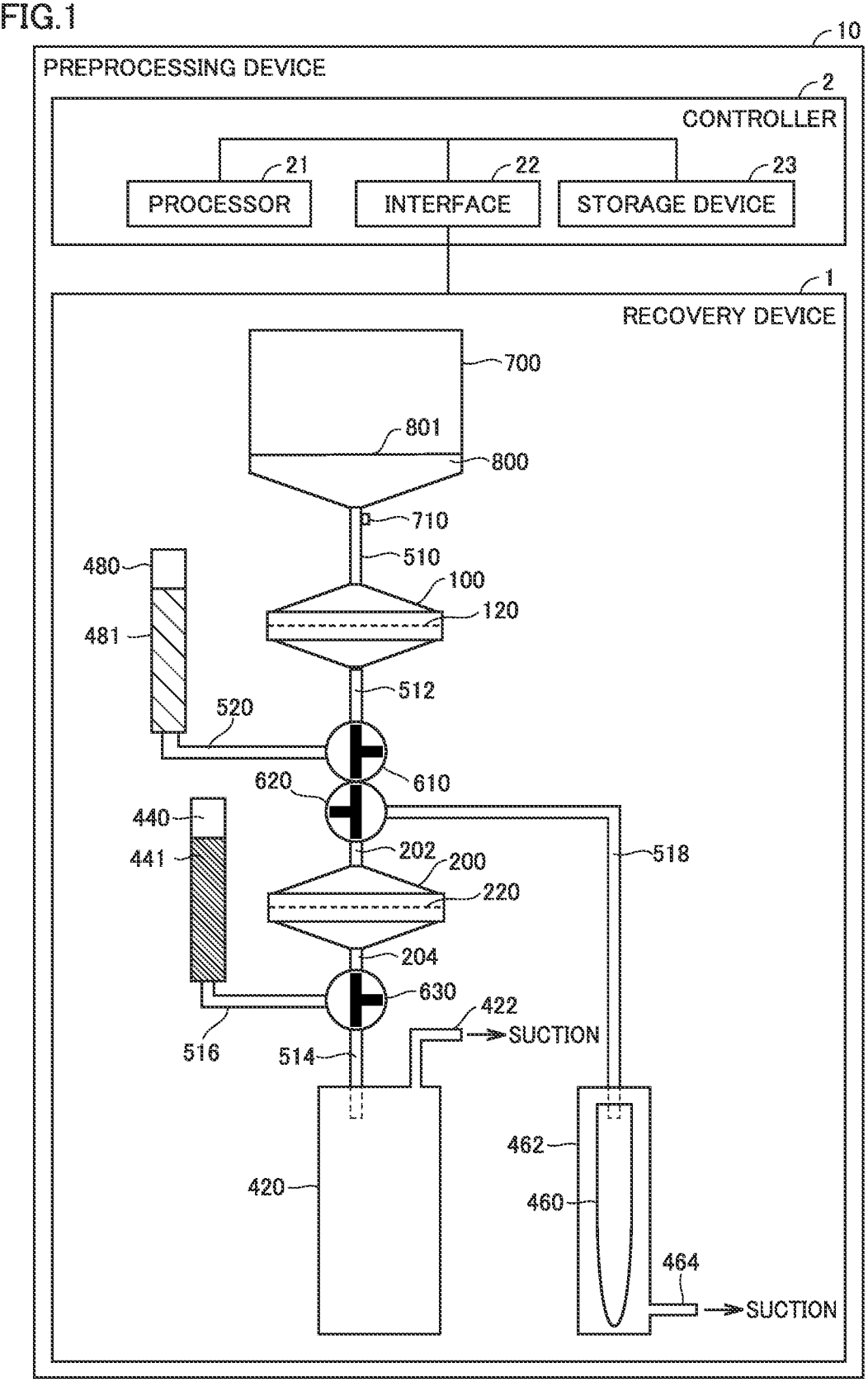
FIG. 1 is a view schematically illustrating an overall configuration of a preprocessing device according to a first embodiment.

With reference to the drawings, embodiments of the present disclosure will be described in detail below. In the drawings, the same or corresponding portion is denoted by the same reference numeral, and the description thereof will not be repeated. In addition, hatched lines in the drawing indicate a liquid component.

For example, the preprocessing device of the present disclosure is used in a preprocessing process in identifying a microorganism in blood. In addition, the preprocessing device of the present disclosure is a device for filtering a liquid sample by a total volume filtration method. In addition, the preprocessing device of the present disclosure is preferably disposable due to a property of aiming at obtaining a microorganism in blood. For example, the microorganism to be recovered in the present disclosure is a bacterium such as a germ and a mycete, viruses, and molds.

First Embodiment

<Configuration of Preprocessing Device>

FIG. 1 is a view schematically illustrating an overall configuration of a preprocessing device according to a first embodiment. As illustrated in FIG. 1, a preprocessing device 10 includes a recovery device 1 and a controller 2 to control recovery device 1. Controller 2 includes a processor 21 to execute calculation in order to control recovery device 1, an interface 22 for communicating with various elements of recovery device 1, and a storage device 23 to store programs and/or data used for calculation of processor 21.

Recovery device 1 includes a sample container 700, a first filter unit 100, a cleaning solution container 480, a first switch 610, a second switch 620, a second filter unit 200, a medium container 440, a third switch 630, a waste liquid container 420, and a recovery container 460.

Each of first switch 610, second switch 620, and third switch 630 switches a flow channel formed in recovery device 1, and is implemented by, for example, a three-way stopcock. Recovery device 1 includes a motor to rotate each of first switch 610, second switch 620, and third switch 630. Controller 2 controls each state of first switch 610, second switch 620, and third switch 630 by controlling driving of each motor. Each of first switch 610, second switch 620, and third switch 630 may be a switch that requires manual operation.

The sample container 700 accommodates a liquid sample 800. In FIG. 1, liquid sample 800 has a liquid level 801.

First filter unit 100 includes a first filter 120 for removing cell membranes such as the blood cell from the liquid sample. The configuration of first filter 120 will be described later.

Cleaning solution container 480 accommodates a cleaning solution for cleaning second filter 220 described later. For example, the cleaning solution may be a buffer solution adjusted to pH that does not kill the microorganisms to be recovered. In one implementation, the cleaning solution is a 20-mM sodium phosphate buffer adjusted to pH 7.2. The preprocessing device need not include the cleaning solution container, but the cleaning solution may be supplied from an external cleaning solution container.

Second filter unit 200 includes a second filter 220 for recovering the microorganism, and further includes a first connection unit 202 and a second connection unit 204. First connection unit 202 and second connection unit 204 face each other with second filter 220 interposed therebetween.

Medium container 440 accommodates a medium 441. Medium 441 is a liquid medium used for culturing the microorganism. The type of medium 441 is selected according to the type of microorganism to be recovered in recovery device 1. An example of medium 441 is a Mueller-Hinton medium. The preprocessing device need not include the medium container, but the medium may be supplied from an external medium container.

Waste liquid container 420 accommodates a waste liquid. A suction unit 422 is provided in an upper portion of waste liquid container 420. Although not illustrated, a vacuum pump is connected to suction unit 422 through a tube or the like. When the vacuum pump is driven, an inside of waste liquid container 420 is decompressed. Waste liquid container 420 is an example of the waste liquid recovery unit. The preprocessing device need not include the waste liquid container, but may be configured to discharge the waste liquid toward the external waste liquid container.

Recovery container 460 accommodates the microorganism recovered from second filter 220 of second filter unit 200. Recovery device 1 further includes a suction box 462 to accommodate recovery container 460. A suction unit 464 is provided on a side surface of suction box 462. Although not illustrated, the vacuum pump is connected to suction unit 464 through a tube or the like. When the vacuum pump is driven, the inside of suction box 462 is decompressed.

Recovery device 1 further includes a sample path 510, a sample path 512, a waste liquid path 514, a medium path 516, a recovery path 518, and a cleaning path 520. Sample path 510 connects sample container 700 to first filter unit 100. Sample path 512 connects first filter unit 100 to first connection unit 202 of second filter unit 200 through first switch 610 and second switch 620. Waste liquid path 514 connects second connection unit 204 of second filter unit 200 and medium container 440 to waste liquid container 420 through third switch 630. Medium path 516 connects medium container 440 to waste liquid container 420 through third switch 630 and waste liquid path 514. Recovery path 518 connects first connection unit 202 of second filter unit 200 to recovery container 460 through second switch 620. Cleaning path 520 connects cleaning solution container 480 to first connection unit 202 of second filter unit 200 through first switch 610 and second switch 620.

A sensor 710 is provided in sample path 510. For example, sensor 710 may be a bubble sensor. Sensor 710 detects the presence or absence of a solution in a portion of sample path 510 to which sensor 710 is attached, and outputs detection output to controller 2.

<First Filter 120>

Figure 2:
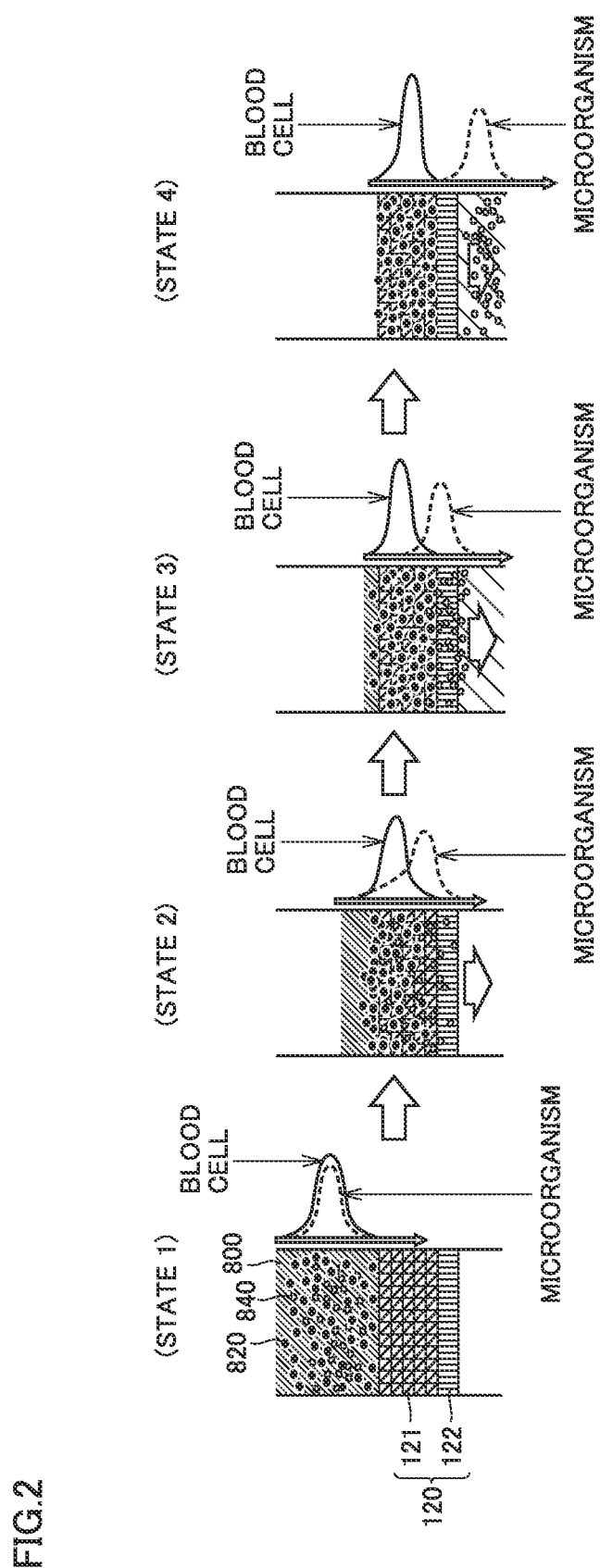
FIG. 2 is a view schematically illustrating movement of a blood cell and a microorganism to be recovered in filtration of a liquid sample in a first filter 120.

FIG. 2 is a view schematically illustrating movement of the blood cell and the microorganism to be recovered in filtration of the liquid sample in first filter 120.

As illustrated in FIG. 2, first filter 120 includes a first layer 121 and a second layer 122. Second layer 122 is provided on a downstream side of first layer 121 (a side to which sample path 512 is connected). First layer 121 is disposed while overlapping second layer 122. Consequently, when sucked from the side of sample path 512, first layer 121 is in close contact with second layer 122.

First layer 121 is configured to permeate the blood cell and a component smaller than the blood cell. When the liquid sample such as whole blood containing the blood cell and the microorganism to be recovered smaller than the blood cell is filtered by first layer 121, the microorganism permeates before the blood cell. At least a part of the microorganisms may permeate through first layer 121 before the blood cells, and a part of the blood cells may permeate through first layer 121 before a part of the microorganisms.

First layer 121 may be a filter for surface filtration or a filter for depth-type filtration as long as first layer 121 is configured to be permeable to the blood cell and the component smaller than the blood cell and has a property of allowing the microorganism to be permeated prior to the blood cell.

First layer 121 has a mechanism that three-dimensionally and temporarily captures the blood cell. Specific examples of the filter having a mechanism that temporarily captures the blood cell include the filter for depth-type filtration. First layer 121 has a path having a diameter that allows the blood cell to pass through the path to permeate through first layer 121 when propulsive force is continuously applied to the blood cell while the blood cell is three-dimensionally and temporarily captured. The components of blood cell mainly include a white blood cell and a red blood cell. The white blood cell is a relatively large particle having a particle diameter of about 10 μm to about 15 μm. The red blood cell has a particle diameter of about 7 μm to about 8 μm. In the blood, the number of red blood cells is the largest in the white blood cells and the red blood cells. Accordingly, the path of first layer 121 preferably has such a diameter as an extent that at least the red blood cell in the white blood cell and the red blood cell can be permeated while three-dimensionally and temporarily captured. Specifically, first layer 121 includes at least the path having the diameter larger than 7 μm. From another viewpoint, first layer 121 has a particle holding ability of 2.7 μm.

First layer 121 may include a hole having a size that can three-dimensionally and temporarily capture a platelet that is contained in the blood and has a particle diameter of about 2 μm.

For example, the filter for depth-type filtration is a depth filter formed by compressing a fibrous material or a porous membrane having a porous structure.

The material of first layer 121 may be any material such as glass, resin, metal, or ceramics. Considering that the blood cell is adsorbed and the path is blocked by the adsorbed blood cell, the material of first layer 121 is desorbed even when the blood cell is adsorbed. For example, first layer 121 is a glass fiber filter or a cellulose filter.

Second layer 122 size-selectively captures blood cell and size-selectively permeates microorganism. Specifically, second layer 122 has a pore having a diameter smaller than the blood cell and larger than the microorganism. For example, the filter diameter of second layer 122 is a diameter having a size capable of removing at least a component larger than or equal to the size of the red blood cell in the blood cell, and for example, is greater than or equal to 2 μm and less than or equal to 6 μm. "Size-selectively captures blood cell and size-selectively permeates microorganism" means that the blood cell is captured in the pore of a filter medium, whereas the microorganism is permeated without being captured in the pore of the filter medium. The microorganism may travel straight by inertial force, collide with the filter medium, and be temporarily captured.

Second layer 122 only needs to be able to remove the blood cell, and may be the filter for surface filtration or the filter for depth-type filtration. When the filter for surface filtration is adopted as second layer 122, the blood cell can be certainly removed as compared with the case of using the filter for depth-type filtration, and a possibility that the blood cell is mixed in filtrate can be decreased.

Examples of the material of second layer 122 include polyethersulfone, cellulose mixed ester, cellulose acetate, nitrocellulose, polytetrafluoroethylene (PTFE), polyvinylidene fluoride (PVDF), polycarbonate, and the like.

<Removal of Blood Cell by First Filter 120>

With reference to FIG. 2 again, the removal of the blood cell from the liquid sample using first filter 120 will be described below.

In the example of FIG. 2, liquid sample 800 includes a blood cell 820 and a microorganism 840. The size of microorganism 840 is smaller than that of blood cell 820. When the microorganism is the bacterium, the size of microorganism 840 is about 1 μm.

For example, liquid sample 800 is a sample after the blood collected from a patient is cultured. Liquid sample 800 may be the blood diluted with another solution.

The graph in FIG. 2 illustrates an example of a concentration distribution in a thickness direction of first filter 120 (first layer 121 and second layer 122). The graph indicated by the solid line illustrates the concentration distribution of the blood cell. The graph indicated by the broken line illustrates the concentration distribution of the microorganism. In FIG. 2, a reference numeral is partially omitted.

FIG. 2 illustrates (state 1) to (state 4). (State 1) represents the state of timing before the filtration. (State 2) and (state 3) indicate the states of timing during the filtration. (State 4) indicates the state after the filtration. That is, the state near first filter 120 changes in order of (state 1) to (state 4).

As illustrated as (state 1), before the filtration, both blood cell 820 and microorganism 840 are dispersed in liquid sample 800.

When suction is performed to start the filtration, first liquid sample 800 permeates through first layer 121. At this time, blood cell 820 collide with the filter medium in the path of first layer 121 and are temporarily captured. On the other hand, microorganism 840 smaller than blood cell 820 is hardly temporarily captured in the path of first layer 121 as compared with blood cell 820. As a result, as illustrated by (state 2) and (state 3), in liquid sample 800, blood cell 820 and microorganism 840 are separated from each other with the lapse of time, and microorganism 840 precedes blood cell 820. Accordingly, microorganism 840 reaches second layer 122 earlier than blood cell 820.

Then, as illustrated as (state 4), the second filtration is performed using second layer 122 while blood cell 820 remains in first layer 121. In second layer 122, only microorganism 840 is size-selectively permeated. Thus, the filtrate from which blood cell 820 is removed while microorganism 840 is left is obtained.

In the example of FIG. 2, first layer 121 filters liquid sample 800, so that the state in which microorganism 840 precedes blood cell 820 with respect to the moving direction of liquid sample 800 is produced. Second layer 122 filters liquid sample 800 while microorganism 840 precede blood cell 820 with respect to the moving direction of liquid sample 800, so that microorganism 840 is permeated through second layer 122 before blood cell 820 is deposited on second layer 122 to generate the clogging. As a result, blood cell 820 can be removed while microorganism 840 in liquid sample 800 is efficiently recovered.

For example, the thickness of first layer 121 can be designed according to the difference between a membrane permeation rate of blood cell 820 and a membrane permeation rate of microorganism 840. More specifically, the thickness of first layer 121 may be designed such that microorganism 840 is permeated through second layer 122 and then blood cell 820 is deposited on second layer 122, and such that blood cell 820 and microorganism 840 are separated. In one example, first layer 121 has the thickness of greater than or equal to 1.3 mm.

Blood cells 820 may not reach second layer 122 at the timing when the whole amount of liquid sample 800 is completely filtered, or all or a part of blood cell 820 may reach second layer 122. First layer 121 performs the first filtration on liquid sample 800 to produce the state in which microorganism 840 precedes blood cell 820, and the microorganism 840 is size-selectively permeated in this state, so that the filtrate from which the blood cell is removed may be obtained without causing clogging during the second filtration.

As described above, first filter 120 is designed such that microorganism 840 permeates through second layer 122 before blood cell 820. Thus, microorganism 840 can permeate through second layer 122 before second layer 122 is clogged by blood cell 820. Accordingly, the microorganism can be efficiently left in the filtrate. Preprocessing device 10 has the configuration that improves recovery efficiency of the microorganism, so that the time required to culture and grow the recovered microorganism to a predetermined number can be shortened.

<Second Filter 220>

Second filter 220 of second filter unit 200 is designed depending on the size of the microorganism to be recovered. For example, when liquid sample 800 flows from first connection unit 202 toward second connection unit 204, the microorganism can be filtered off from liquid sample 800 by second filter 220. Preprocessing device 10 is configured to directly recover the microorganism filtered off by second filter unit 200 in medium 441, so that the recovery efficiency of the microorganism can be improved. Preprocessing device 10 has the configuration that improves the recovery efficiency of the microorganism, so that the time required to culture and grow the recovered microorganisms to the predetermined number can be shortened.

Second filter 220 only needs to be able to filter out the microorganism to be recovered, and may be the filter for surface filtration or the filter for depth-type filtration. The microorganism is deposited on second filter 220 when the filter for surface filtration is adopted as second filter 220, whereas the microorganism is trapped inside the filter when the filter for depth-type filtration is adopted as second filter 220. Accordingly, it is expected that the microorganism is easily recovered when the filter for surface filtration is adopted as second filter 220 as compared with the filter for depth filtration is adopted.

When the microorganism to be recovered is the bacterium, for example, second filter 220 is a general sterilizing filter having a nominal pore diameter of 0.2 µm to 3.00 µm.

In recovery device 1, when first filter 120 and second filter 220 are designed depending on the above-described conditions, the bubble point of second filter 220 tends to be higher than the bubble point of first filter 120 (first layer 121 and second layer 122 are generally named). In one example, the bubble point of first filter 120 is about 20 kPa, whereas the bubble point of second filter 220 is about 50 kPa.

<Recovery Method>

Figure 3:
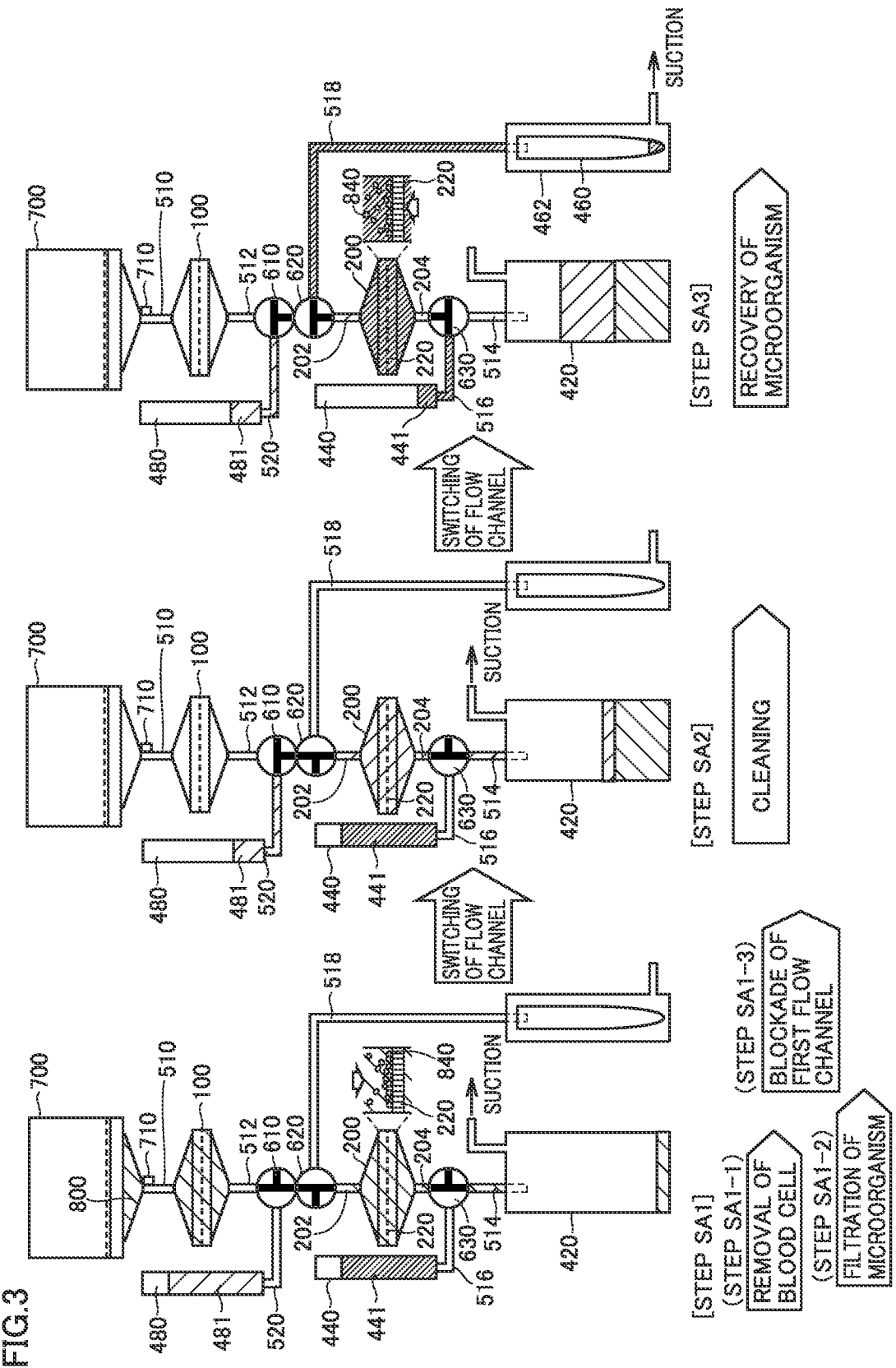
FIG. 3 is a view schematically illustrating an example of a flow of a microorganism recovery method using a preprocessing device 10 of the first embodiment.

FIG. 3 is a view schematically illustrating an example of a flow of a microorganism recovery method using preprocessing device 10 of the first embodiment. FIG. 3 illustrates three stages (steps SA1, SA2, SA3) in the microorganism recovery method. With reference to FIG. 3, the flow of the microorganism recovery method will be described.

(Filtration of Microorganism)

First, as illustrated as step SA1, microorganism 840 is filtered off from liquid sample 800. In step SA1, second filter unit 200 is connected to sample path 512 and waste liquid path 514. That is, first switch 610 and second switch 620 are controlled to connect first connection unit 202 of second filter unit 200 to sample path 512, and third switch 630 is controlled to connect second connection unit 204 of second filter unit 200 to waste liquid path 514.

In the present specification, the flow channel formed in recovery device 1 in step SA1 is referred to as a "first flow channel". Following the first flow channel, liquid sample 800 sequentially passes through sample container 700, sample path 510, first filter unit 100 (first filter 120), sample path 512, first switch 610, second switch 620, second filter unit 200 (first connection unit 202, second filter 220, second connection unit 204), third switch 630, and waste liquid path 514, and is accommodated in waste liquid container 420.

In this state, when the inside of waste liquid container 420 is decompressed by driving of the vacuum pump, liquid sample 800 in sample container 700 is sucked and passes through first filter unit 100 and second filter unit 200. Thus, a substance to be removed such as the blood cell is removed from the liquid sample by first filter unit 100 (step SA1-1), and microorganism 840 is filtered off from liquid sample 800 by second filter unit 200 (step SA1-2).

(Blockade of First Flow Channel)

When sensor 710 detects that the solution runs out in sample path 510 while the first flow channel is formed in preprocessing device 10, controller 2 blocks the first flow channel (step SA1-3). In one example, controller 2 controls first switch 610 to cut off first connection unit 202 from sample path 512, thereby blocking the first flow channel.

In the first flow channel, sensor 710 is disposed upstream second filter unit 200 (first connection unit 202). The first flow channel is cut off in response to sensor 710 detecting that the solution runs out in sample path 510, whereby the air is prevented from flowing into second filter unit 200 through first connection unit 202.

In cutting off the first flow channel, the flow channel formed in recovery device 1 may be changed from the first flow channel to the second flow channel described later.

(Cleaning)

Subsequently, as illustrated as step SA2, second filter unit 200 is cleaned with the cleaning solution in cleaning solution container 480. In step SA2, second filter unit 200 is connected to cleaning path 520 and waste liquid path 514. That is, first switch 610 is controlled to disconnect first connection unit 202 from sample path 512 and connect first connection unit 202 to cleaning path 520. Second switch 620 is controlled to connect first connection unit 202 to cleaning path 520. Third switch 630 is controlled to connect second connection unit 204 to waste liquid path 514.

In the present specification, the flow channel formed in recovery device 1 in step SA2 is referred to as a "second flow channel". Following the second flow channel, a cleaning solution 481 sequentially passes through cleaning solution container 480, cleaning path 520, first switch 610, second switch 620, second filter unit 200 (first connection unit 202, second filter 220, second connection unit 204), third switch 630, and waste liquid path 514, and is accommodated in waste liquid container 420.

In step SA2, the inside of waste liquid container 420 is decompressed by driving of the vacuum pump while the second flow channel is formed. Thus, cleaning solution 481 in cleaning solution container 480 is sucked and passes through second filter unit 200. Consequently, second filter 220 in second filter unit 200 is cleaned with cleaning solution 481.

(Recovery of Microorganism)

Subsequently, as illustrated as step SA3, microorganism 840 filtered off by second filter unit 200 is recovered together with medium 441. In step SA3, second filter unit 200 is connected to medium container 440 and recovery container 460. That is, third switch 630 is controlled to connect second connection unit 204 to medium path 516. Second switch 620 is controlled to connect first connection unit 202 to recovery path 518.

In the present specification, the flow channel formed in recovery device 1 in step SA3 is referred to as a "third flow channel". Following the third flow channel, medium 441 sequentially passes through medium container 440, medium path 516, third switch 630, second filter unit 200 (second connection unit 204, second filter 220, first connection unit 202), and recovery path 518, and is accommodated in recovery container 460.

In step SA3, the inside of suction box 462 is decompressed by driving of the vacuum pump while the third flow channel is formed. Thus, medium 441 in medium container 440 is sucked and passes through second filter unit 200. Thus, the microorganism deposited on second filter 220 in second filter unit 200 is recovered in recovery container 460 together with medium 441.

In the example of FIG. 3, each of the filtration of the microorganism in step SA1, the cleaning of second filter 220 in step SA2, and the recovery of the microorganism in step SA3 was promoted by the decompression. That is, in the filtration, the suction of liquid sample 800 is promoted by the decompression of waste liquid container 420. In the above cleaning, the flow of cleaning solution 481 is promoted by the decompression of waste liquid container 420. In the recovery, the flow of medium 441 is promoted by the decompression of recovery container 460.

Each of the filtration, the cleaning, and the recovery may be promoted by pressurization. For example, in the filtration separation, the suction of liquid sample 800 may be promoted by pressurizing sample container 700 instead of the decompression of waste liquid container 420 or in addition to the decompression of waste liquid container 420. For example, in the cleaning, the flow of cleaning solution 481 may be promoted by pressurization of cleaning solution container 480 instead of the decompression of waste liquid container 420 or in addition to the decompression of waste liquid container 420. For example, in the recovery, the flow of medium 441 may be promoted by pressurization of medium container 440 in addition to the decompression of recovery container 460 or in addition to the decompression of recovery container 460.

<Processing Flow>

Figure 4:
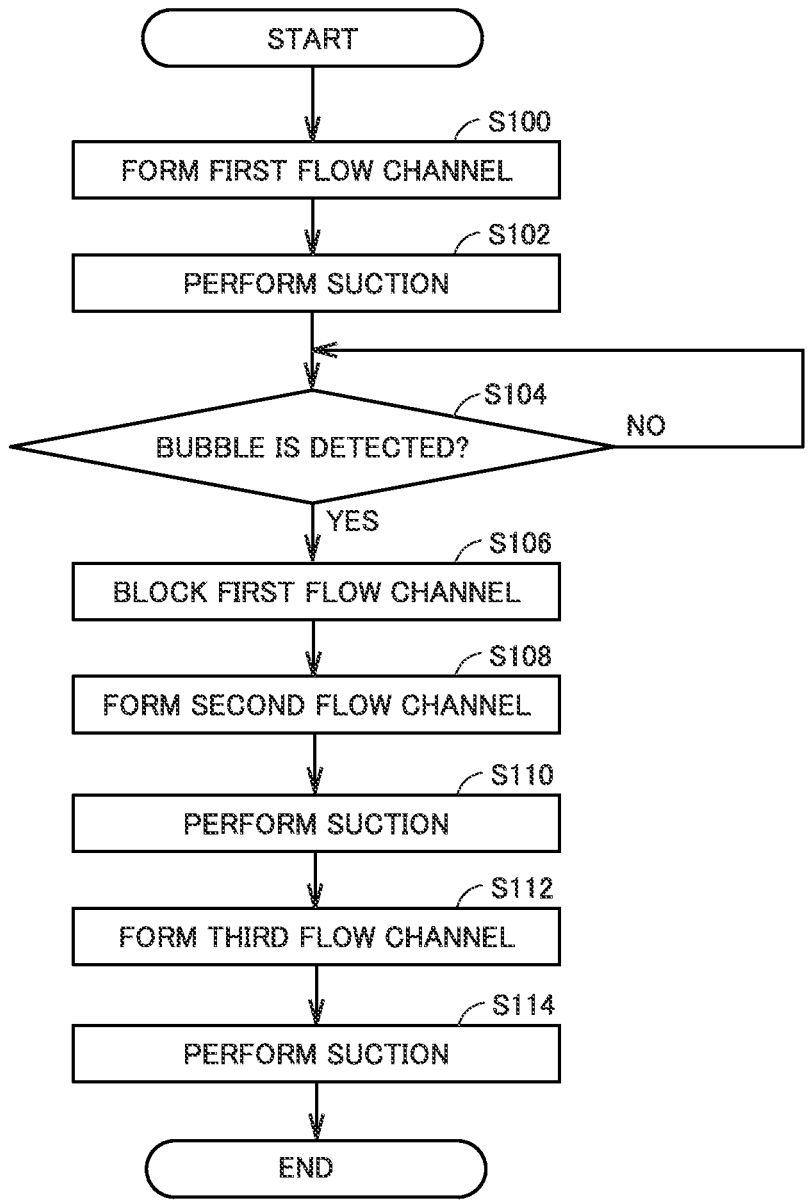
FIG. 4 is a view illustrating an example of processing executed by a controller 2 to implement the microorganism recovery method in FIG. 3 in the preprocessing device 10.

FIG. 4 is a view illustrating an example of processing executed by controller 2 to implement the microorganism recovery method indicated as steps SA1 to SA3 in FIG. 3 in preprocessing device 10. In one implementation, controller 2 implements the processing of FIG. 4 by processor 21 executing a given program.

In step S100, controller 2 causes recovery device 1 to form the first flow channel (step SA1 in FIG. 3). More specifically, controller 2 drives the motors of first switch 610, second switch 620, and third switch 630 to form the first flow channel.

In step S102, controller 2 instructs the vacuum pump connected to waste liquid container 420 to be driven, thereby sucking liquid sample 800 for the filtration in step SA1.

In step S104, controller 2 determines whether sensor 710 detects the bubble in sample path 510. Controller 2 repeats the control in step S104 until it is determined that the bubble is detected by sensor 710 (NO in step S104). When determining that the bubble is detected by sensor 710 (YES in step S104), controller 2 advances the control to step S106.

In step S106, controller 2 blocks the first flow channel.

In step S108, controller 2 causes recovery device 1 to form the second flow channel (step SA2 in FIG. 3). More specifically, controller 2 drives the motors of first switch 610, second switch 620, and third switch 630 to form the second flow channel.

In the process of FIG. 4, step S106 and step S108 may be simultaneously executed. That is, controller 2 may form the second flow channel by blocking the first flow channel in step S106. In the second flow channel, the flow channel between first connection unit 202 and sample path 512 is cut off, so that second filter unit 200 is separated from sample container 700, whereby the first flow channel is blocked. Accordingly, the first flow channel can be blocked and the second flow channel can be formed at the same time.

In step S110, controller 2 instructs the vacuum pump connected to waste liquid container 420 to be driven, thereby sucking cleaning solution 481 for the cleaning in step SA2. After a predetermined time or amount of suction is performed, controller 2 advances the control to step S112.

In step S112, controller 2 causes recovery device 1 to form the third flow channel (step SA3 in FIG. 3). More specifically, controller 2 drives the motors of first switch 610, second switch 620, and third switch 630 to form the third flow channel.

In step S114, controller 2 instructs the vacuum pump connected to suction box 462 to be driven, thereby sucking medium 441 for the recovery in step SA3. After a predetermined time or amount of suction is performed, controller 2 terminates the processing in FIG. 4.

When it is detected that the bubble is mixed in sample path 510, the first flow channel is blocked. Thus, the situation in which the air is mixed into second filter unit 200 to enter the upper portion of second filter 220 can be avoided.

In recovery device 1, when liquid sample 800 disappears in sample container 700, the bubble is mixed into sample path 510. Accordingly, the detection of the bubble by sensor 710 means detection of a decrease (for example, the remaining amount is below a predetermined value) in the remaining amount of liquid sample 800 upstream second filter unit 200 of the first flow channel. In the processing of FIG. 4, controller 2 causes first switch 610 to block the first flow channel in response to the detection of the bubbles by sensor 710. In this sense, sensor 710, controller 2, and first switch 610 are examples of the blocking element in preprocessing device 10. In the first flow channel, a portion where the flow channel is switched by first switch 610 is an example of the "predetermined portion".

Second Embodiment

Figure 5:
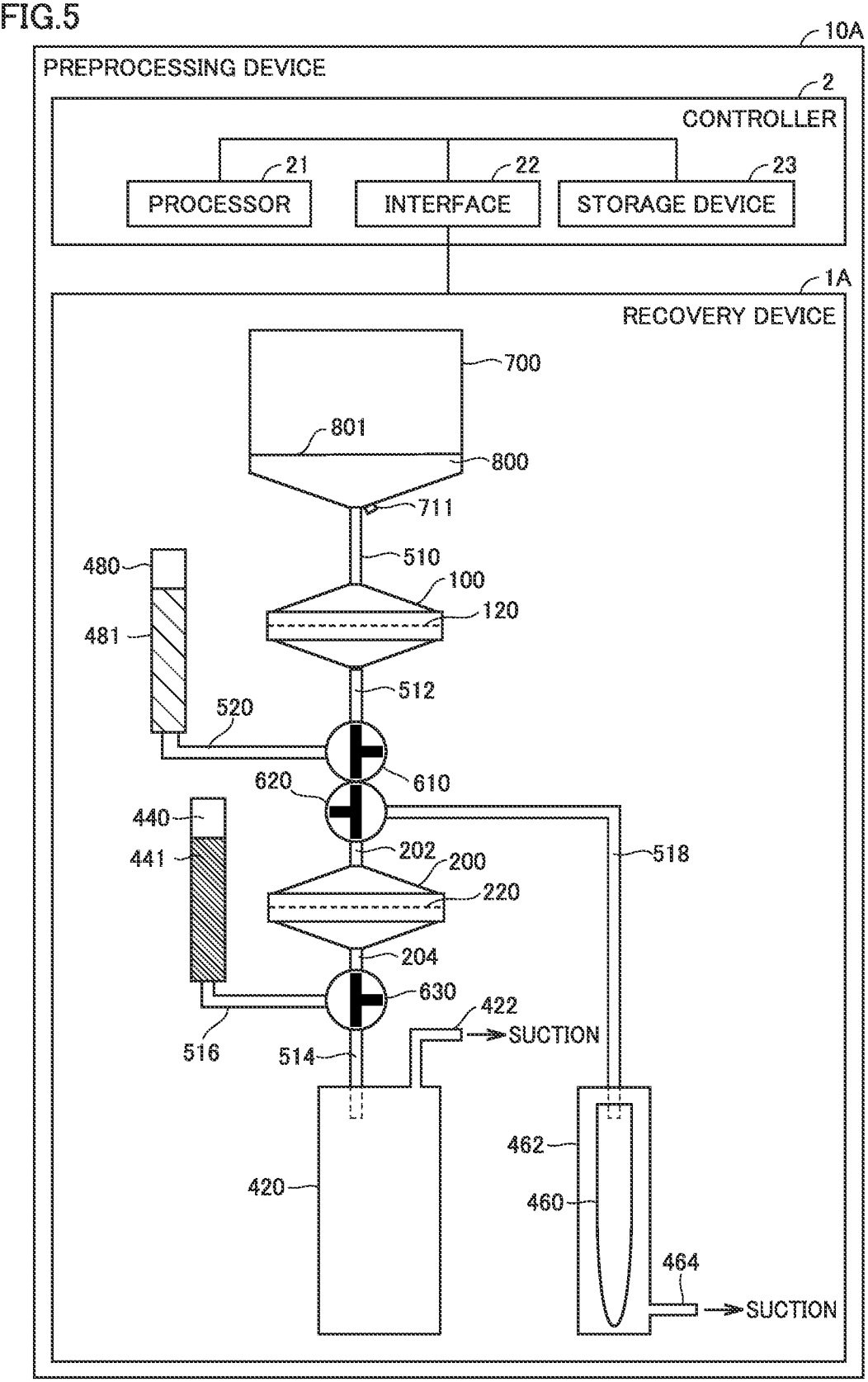
FIG. 5 is a view schematically illustrating an overall configuration of a preprocessing device according to a second embodiment.

FIG. 5 is a view schematically illustrating an overall configuration of a preprocessing device according to a second embodiment. As compared with recovery device 1 of preprocessing device 10 of the first embodiment, a recovery device 1A of a preprocessing device 10A of the second embodiment includes a sensor 711 instead of sensor 710. Sensor 711 detects the remaining amount of liquid sample 800 in sample container 700. For example, sensor 711 detects whether the liquid level of liquid sample 800 in sample container 700 lowers and reaches a predetermined value. That is, sensor 711 detects that the remaining amount of liquid sample 800 in sample container 700 becomes less than or equal to the predetermined value. Sensor 711 transmits detection output to controller 2.

Figure 6:
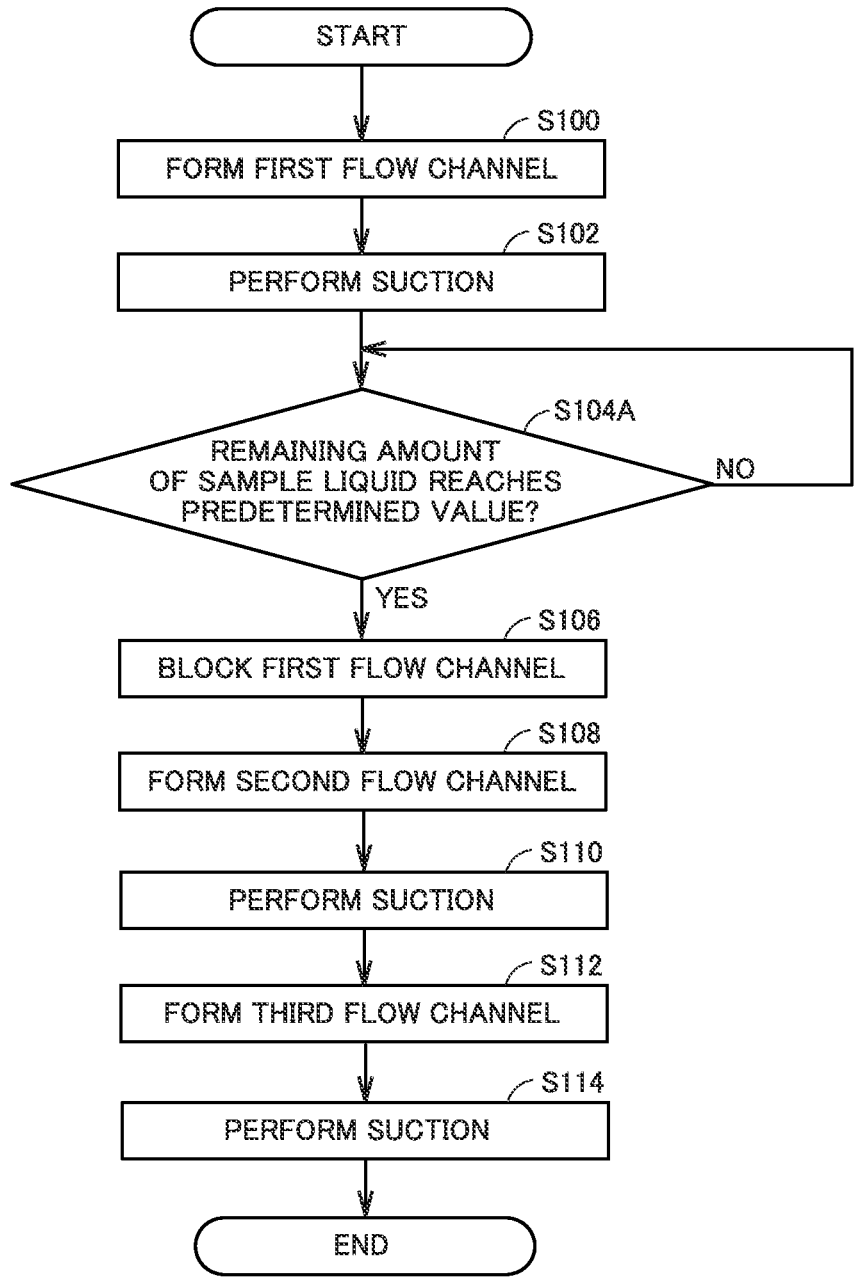
FIG. 6 is a view illustrating an example of a modification of the processing in FIG. 4.

FIG. 6 is a view illustrating an example of a modification of the processing in FIG. 4. The processing in FIG. 6 includes step S104A instead of step S104 as compared with the processing in FIG. 4. After step S102, controller 2 proceeds with the control to step S104A.

In step S104A, controller 2 uses sensor 711 to determine whether the remaining amount of liquid sample 800 in sample container 700 reaches the predetermined value. Controller 2 repeats the control of step S104A until it is determined that the remaining amount reaches the predetermined value (NO in step S104A). When controller 2 determines that the remaining amount reaches the predetermined value, controller 2 blocks the first flow channel in step S106.

In the second embodiment described above, the first flow channel is blocked in accordance with a decrease in the remaining amount of liquid sample 800 in sample container 700. That is, in the second embodiment, as compared with the first embodiment, the first flow channel is blocked according to the detection result upstream of the position of sensor 710. Thus, the situation in which the air is mixed into second filter unit 200 to enter the upper portion of second filter 220 can be more reliably avoided.

Third Embodiment

Figure 7:
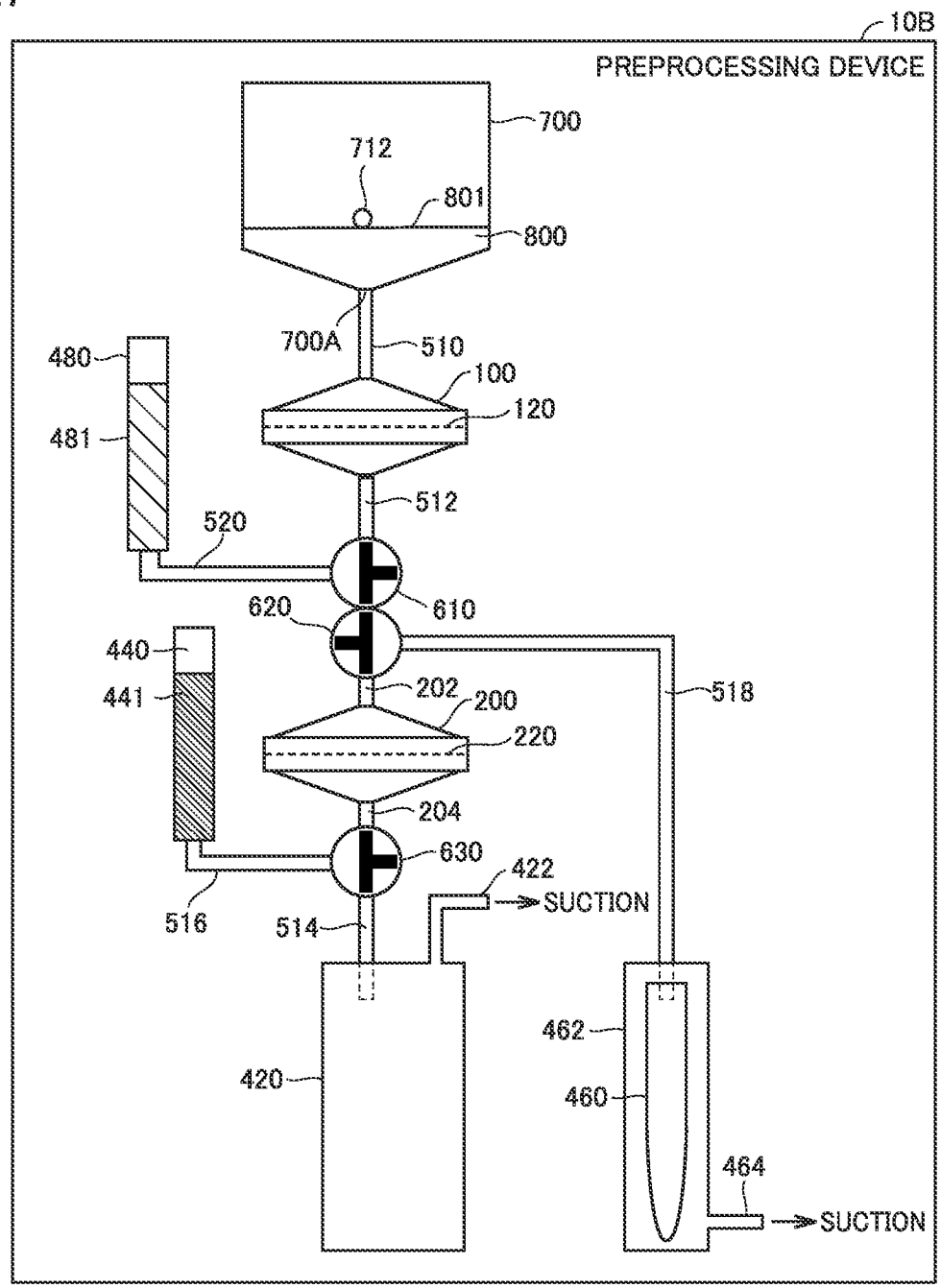
FIG. 7 is a view schematically illustrating an overall configuration of a preprocessing device according to a third embodiment.

FIG. 7 is a view schematically illustrating an overall configuration of a preprocessing device according to a third embodiment. As compared with preprocessing device 10 of the first embodiment, a preprocessing device 10B of the third embodiment does not include controller 2 and sensor 710, but includes a float valve 712. FIG. 7 illustrates an opening 700A in sample container 700. Sample container 700 is connected to sample path 510 at opening 700A. Liquid sample 800 accommodated in sample container 700 flows into sample path 510 through opening 700A.

Figure 8:
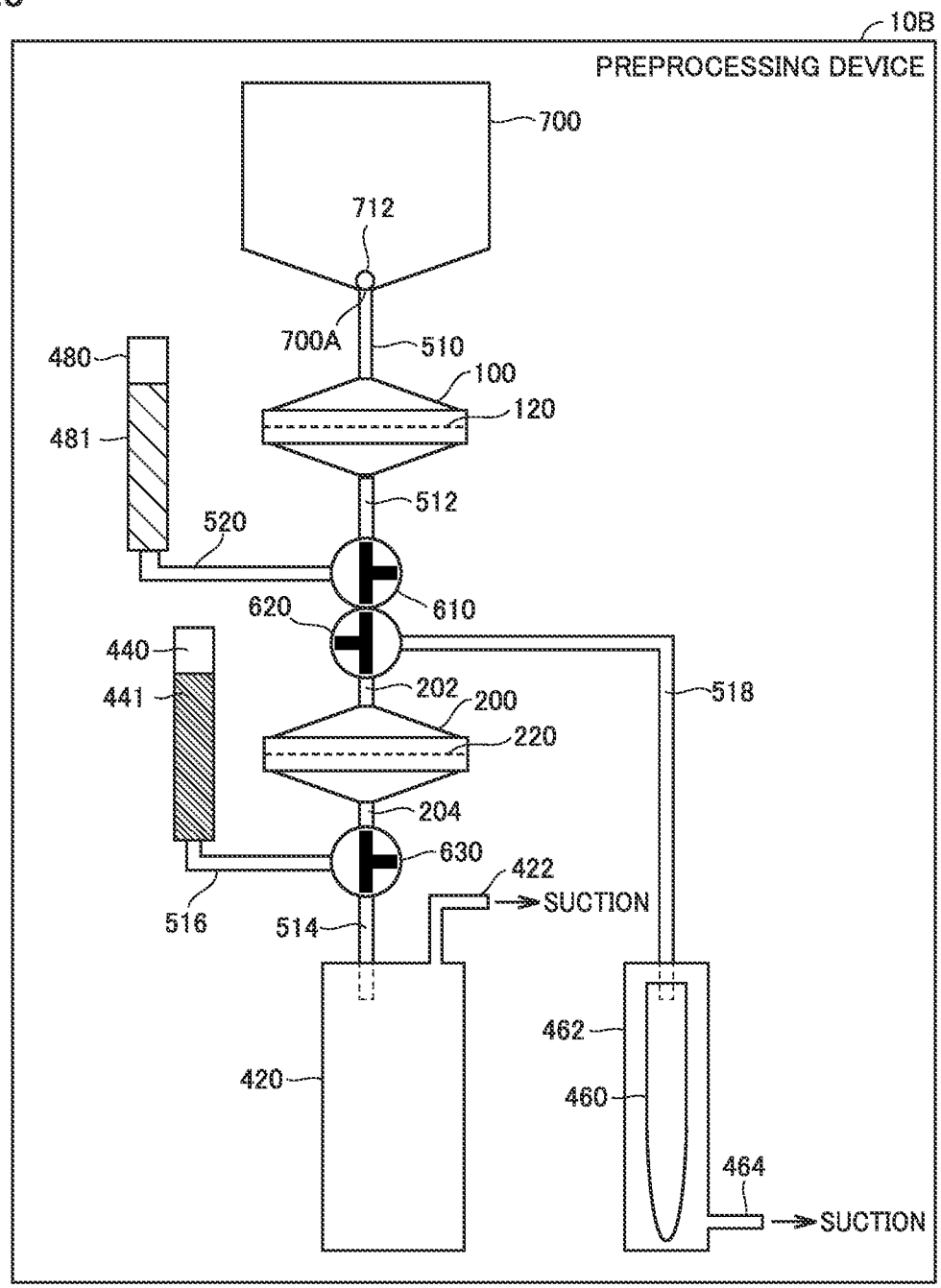
FIG. 8 is a view illustrating a state in which the liquid sample runs out in a sample container 700.

FIG. 8 is a view illustrating the state in which the liquid sample runs out in sample container 700. As illustrated in FIG. 8, float valve 712 floats on the liquid sample in sample container 700, moves with the liquid level, and closes opening 700A when the liquid sample runs out.

In the third embodiment, float valve 712 is an example of a member that changes the state so as to close opening 700A according to a decrease (for example, the remaining amount is less than or equal to the predetermined value) in the remaining amount of the liquid sample in the sample container. The member may be implemented as a check valve provided in opening 700A.

Fourth Embodiment

<Configuration of Preprocessing Device>

Figure 9:
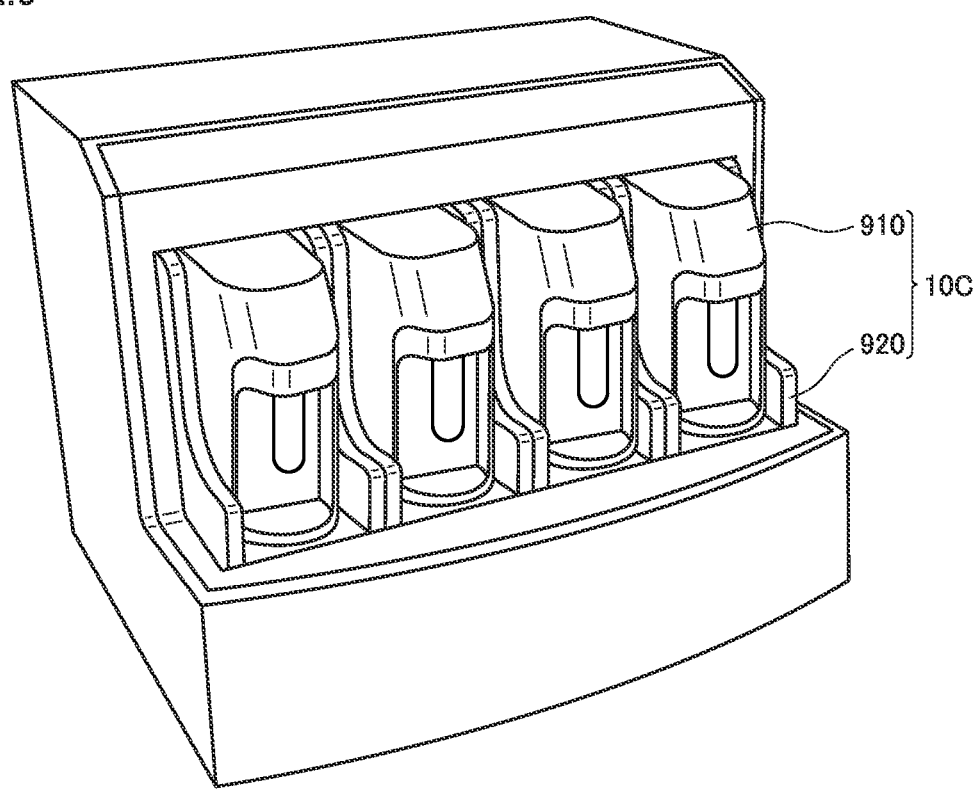
FIG. 9 is a schematic perspective view illustrating a preprocessing device according to a fourth embodiment.

FIG. 9 is a schematic perspective view illustrating a preprocessing device according to a fourth embodiment. A preprocessing device 10C of the fourth embodiment further includes a housing 910 and an accommodating body 920 as compared with preprocessing device 10 of the first embodiment. In FIG. 9, a unit in which four preprocessing devices 10C are integrated is disclosed, and the reference numeral is partially omitted.

Figure 10:
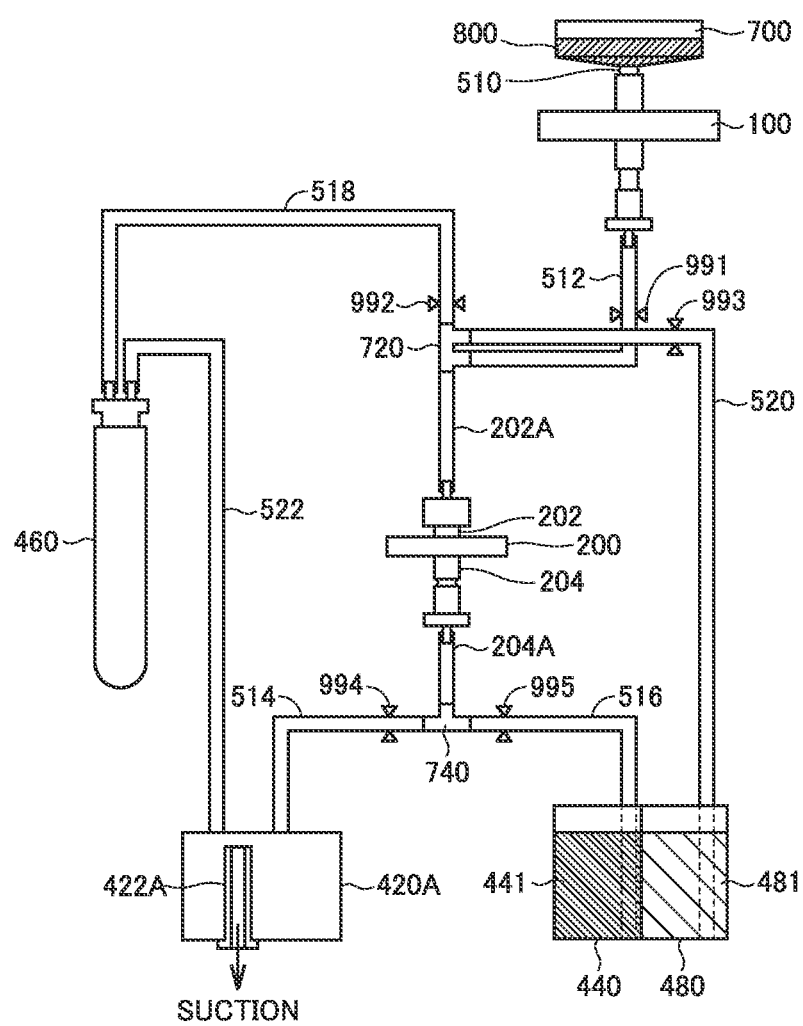
FIG. 10 is a view schematically illustrating a configuration of a recovery device portion of the preprocessing device of the fourth embodiment.

FIG. 10 is a view schematically illustrating a configuration of a recovery device portion of the preprocessing device of the fourth embodiment. In a recovery device 1C constituting preprocessing device 10C of the fourth embodiment, at least a part of the flow channel such as the first flow channel (a portion that cross an opening described later in sample path 512, waste liquid path 514, medium path 516, recovery path 518, and cleaning path 520) is made of a material having plasticity. Recovery device 1C includes five pinch valves 991 to 995 instead of first switch 610, second switch 620, and third switch 630 of the first embodiment. Each of pinch valves 991 to 995 cuts off the flow of the solution in the tube by pressing the portion of the flow channel. Each of pinch valves 991 to 995 allows the flow of the solution in the portion of the flow channel by releasing the pressure. That is, each of pinch valves 991 to 995 opens and closes the portion of the flow channel. Controller 2 controls opening and closing of each of pinch valves 991 to 995.

Recovery device 1C further includes a suction path 522, a first connector 720, and a second connector 740. Recovery device 1C includes a waste liquid container 420A instead of waste liquid container 420 and suction box 462 of the first embodiment. Waste liquid container 420A includes a suction unit 422A. A vacuum pump is connected to suction unit 422A. When the vacuum pump is driven, the inside of waste liquid container 420A is decompressed.

First connection unit 202 of second filter unit 200 is connected to sample path 512, recovery path 518, and cleaning path 520 through a tube 202A and first connector 720.

The junction (connection point with first connector 720) of sample path 512 and first connection unit 202 is preferably closer to second filter unit 200 than the junction (connection point with first connector 720) of cleaning path 520 and first connection unit 202. With this configuration, in the cleaning using cleaning solution 481, liquid sample 800 remaining in first connector 720 is more reliably washed off, and the generation of contamination in medium 441 can be prevented.

The junction (connection point with first connector 720) between recovery path 518 and first connection unit 202 may be disposed at a position closer to second filter unit 200 than the junction (connection point with first connector 720) between cleaning path 520 and first connection unit 202. With this configuration, because medium 441 passes through at least the flow channel through which cleaning solution 481 passes among the flow channels through which liquid sample 800 passes, the generation of the contamination in medium 441 can be prevented.

Second connection unit 204 of second filter unit 200 is connected to waste liquid path 514 and medium path 516 through tube 204A and second connector 740.

Each of first connector 720 and second connector 740 does not have a function of switching the flow channel, but merely has a function of branching the flow channel. Each of first connection unit 202 and second connection unit 204 is an example of each of the first connection unit and the second connection unit. As long as the flow channels extending from the first connection unit and the second connection unit are branched, the branching method is not limited to the provision of first connector 720 and second connector 740.

<Formation of First to Third Flow Channels>

Formation of the first to third flow channels (FIG. 3) in recovery device 1C in FIG. 10 will be described.

(First Flow Channel) In order to form the first flow channel, in recovery device 1C, pinch valves 991, 994 are opened and pinch valves 992, 993, 995 are closed.

When the inside of waste liquid container 420A is decompressed while the first flow channel is formed, liquid sample 800 in sample container 700 is filtered by first filter unit 100 and second filter unit 200.

(Second Flow Channel) In order to form the second flow channel, in recovery device 1C, pinch valves 993, 994 are opened and pinch valves 991, 992, 995 are closed.

When the inside of waste liquid container 420A is decompressed while the second flow channel is formed, second filter 220 in second filter unit 200 is cleaned with cleaning solution 481.

(Third Flow Channel)

In order to form the third flow channel, in recovery device 1C, pinch valves 992, 995 are opened and pinch valves 991, 993, 994 are closed.

When the inside of waste liquid container 420A is depressurized while the third flow channel is formed, the microorganisms deposited on second filter 220 are recovered by recovery container 460 together with medium 441.

<Blockage of First Flow Channel>

In recovery device 1C of FIG. 10, the first flow channel is blocked by closing at least pinch valve 991. The first flow channel is blocked even in the state where the second flow channel (or the third flow channel) is formed.

In the fourth embodiment, in response to the detection output of sensor 710 (and/or sensor 711), controller 2 may close pinch valve 911 to block the first flow channel. In this sense, in the fourth embodiment, sensor 710 (and/or sensor 711), pinch valve 911, and controller 2 constitute the blocking element.

<Configuration of Housing>

Figure 11:
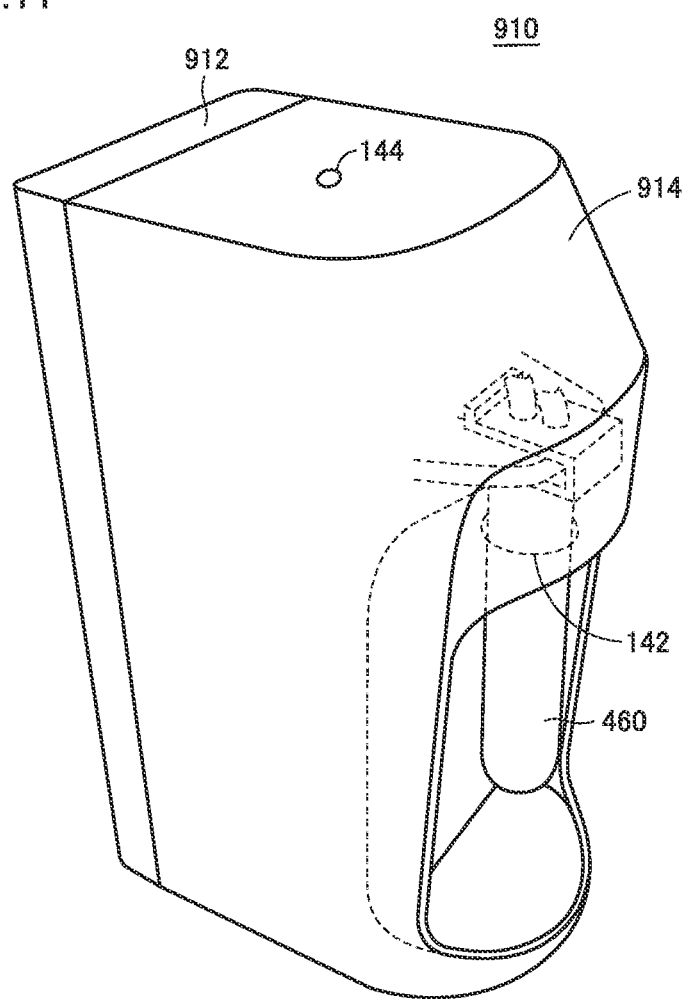
FIG. 11 is a schematic perspective view illustrating a housing in FIG. 9.
Figure 12:
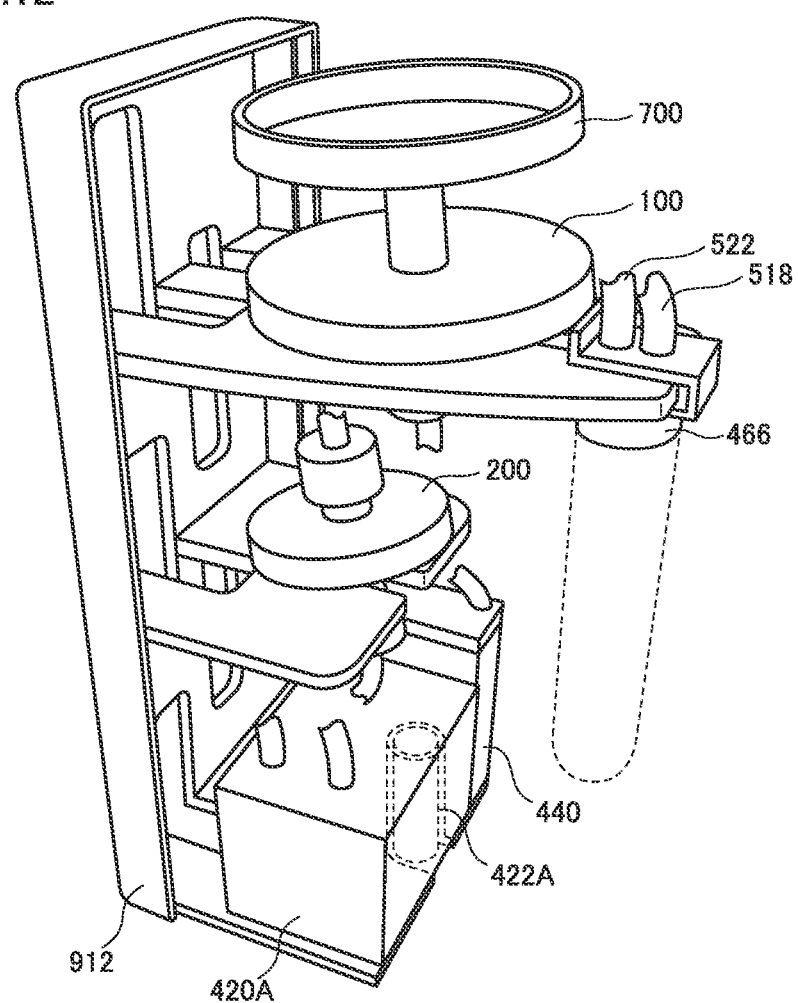
FIG. 12 is a schematic perspective view illustrating a state in which a cover is removed from the housing in FIG. 11.
Figure 13:
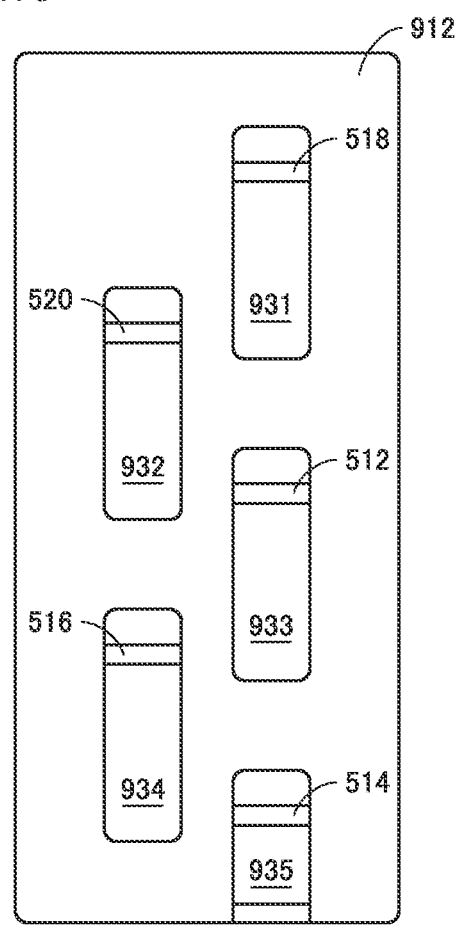
FIG. 13 is a schematic rear view illustrating the housing in FIG. 11.

FIG. 11 is a schematic perspective view illustrating the housing in FIG. 9. FIG. 12 is a schematic perspective view illustrating a state in which a cover is removed from the housing in FIG. 11. FIG. 13 is a schematic rear view illustrating the housing in FIG. 11. In FIG. 11, a part hidden by cover 914 is indicated by a broken line. Furthermore, in FIG. 12, in order to simplify the illustration, the description of the flow channel connecting each container and the filter unit is omitted.

Referring to FIG. 11, housing 910 includes a main body 912 and a cover 914 attached to main body 912. A connection unit 142 and an injection port 144 are formed in cover 914 in order to receive liquid sample 800.

In housing 910, a connection unit 466 (see FIG. 12) is disposed at a position facing connection unit 142. Recovery path 518 and suction path 522 are fixed to connection unit 466.

Recovery container 460 has one end opened and is configured to be detachably attached to connection unit 466. Recovery container 460 has a size that can be inserted into housing 910 through connection unit 142, and can be attached to connection unit 466 disposed in housing 910 through connection unit 142 or can be detached from connection unit 466. Accordingly, recovery container 460 is detachably supported by housing 910.

In housing 910, sample container 700 is disposed at a position facing injection port 144 formed in cover 914. For this reason, liquid sample 800 injected from injection port 144 is accommodated in sample container 700.

As illustrated in FIGS. 11 and 12, at least a part of recovery container 460 is exposed from housing 910. On the other hand, sample container 700, first filter unit 100, second filter unit 200, waste liquid container 420A, medium container 440, cleaning solution container 480 (not illustrated), and the flow channel connecting these units are all accommodated in housing 910. Accordingly, a portion touched by a human hand can be minimized, contamination is hardly generated, and infection from liquid sample 800 can be prevented.

Referring to FIG. 12, sample container 700, first filter unit 100, second filter unit 200, waste liquid container 420A, medium container 440, cleaning solution container 480, and connection unit 466 are disposed in main body 912.

Referring to FIG. 13, five connection units 931 to 935 are formed on the back surface of main body 912. Recovery path 518 is disposed on main body 912 so as to cross connection unit 931. Cleaning path 520 is disposed in main body 912 so as to cross connection unit 932. Sample path 512 is disposed in main body 912 so as to cross connection unit 933. Medium path 516 is disposed in main body 912 so as to cross connection unit 934. Waste liquid path 514 is disposed in main body 912 so as to cross connection unit 935.

Among recovery path 518, cleaning path 520, sample path 512, medium path 516, and waste liquid path 514, at least a portion crossing each of connection units 931 to 935 is constituted by a tube having plasticity.

<Configuration of Accommodating Body>

Figure 14:
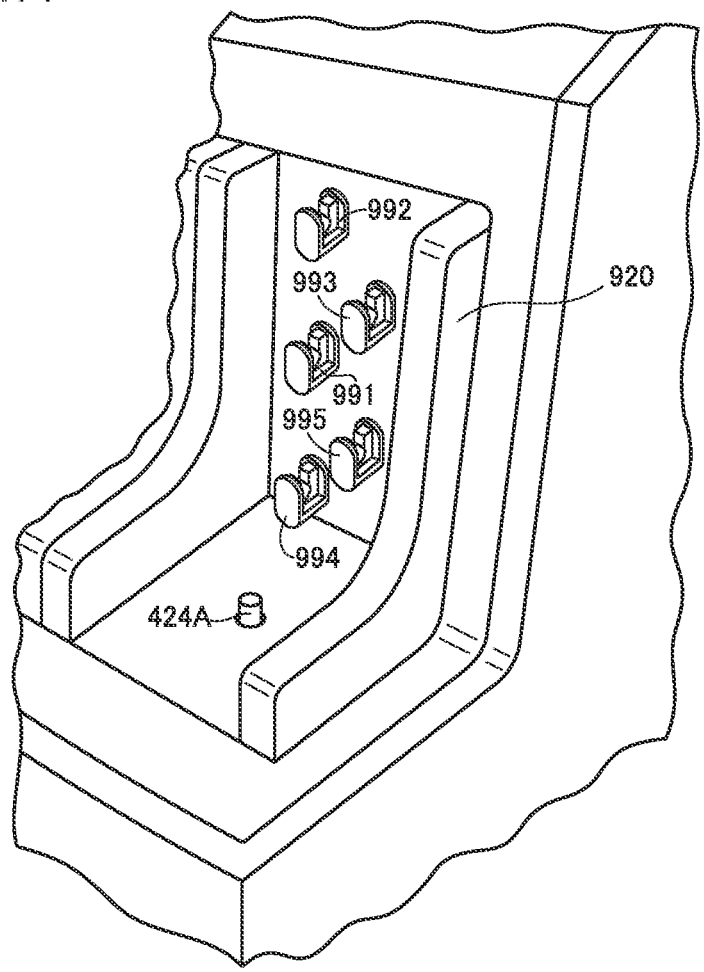
FIG. 14 is a schematic perspective view illustrating an accommodating body in FIG. 9.

FIG. 14 is a schematic perspective view illustrating the accommodating body in FIG. 9. With reference to FIG. 14, pinch valves 991 to 995 and a suction tube 424A are disposed in accommodating body 920. Suction unit 422A (FIGS. 10 and 12) is connected to the vacuum pump through suction tube 424A.

Each of pinch valves 992, 993, 991, 995, 994 is disposed on a surface facing the back surface of main body 912 on which each of connection units 931, 932, 933, 934, 935 is formed when housing 910 is attached to accommodating body 920.

With this disposition, when housing 910 is attached to accommodating body 920, recovery path 518 crossing connection unit 931 is sandwiched by pinch valve 992.

Similarly, cleaning path 520 crossing connection unit 932 is sandwiched by pinch valve 993. Sample path 512 crossing connection unit 933 is sandwiched by pinch valve 991. Medium path 516 crossing connection unit 934 is sandwiched by pinch valve 995. Pinch valve 994 sandwiches waste liquid path 514 crossing connection unit 935.

Since accommodating body 920 and housing 910 are configured as described above, the desired switch is attached to each flow channel as illustrated in FIG. 10 when housing 910 is attached to accommodating body 920.

Further, suction tube 424A is provided at a position facing a surface (bottom surface) where suction unit 422A of waste liquid container 420A accommodated in housing 910 is located when housing 910 is attached to accommodating body 920. Thus, when housing 910 is attached to accommodating body 920, suction tube 424A can be attached to suction unit 422A.

The switch (pinch valves 991 to 995) that switches the flow channel needs to be controlled by controller 2 in order to automate the recovery of the microorganism. On the other hand, each flow channel switched by the switch is contaminated by liquid sample 800 or the like, is hardly repeatedly used. For this reason, preferably each channel is discarded every time of use.

Accordingly, when the switch and the flow channel are integrally formed, it is necessary to discard the switch together with the flow channel, and when the switch and controller 2 are used a plurality of times, it is necessary to connect the switch and controller 2 each time, or cost increases.

In preprocessing device 10C of the fourth embodiment, the switch (pinch valves 991 to 995) switching the flow channel is configured to sandwich the flow channel from the outside. Consequently, the switch and the flow channel can be separated. Thus, in automating the recovery of the microorganism, the component that is required to be controlled by the controller and the component that is contaminated by liquid sample 800 or the like can be separated, and usability is improved when the component that is required to be controlled by the controller is used a plurality of times.

In addition, preprocessing device 10C of the fourth embodiment is disposed in accommodating body 920 such that each switch switching the flow channel is attached to the corresponding flow channel when housing 910 is attached to accommodating body 920. Accordingly, the user can use preprocessing device 10C only by attaching or detaching housing 910 that cannot be reused to or from accommodating body 920.

In preprocessing device 10C of the fourth embodiment, sample container 700, first filter unit 100, second filter unit 200, waste liquid container 420A, medium container 440, cleaning solution container 480 (not illustrated), and the flow channel connecting these units are all accommodated in housing 910. At least a portion (pipe) to which each switch is attached in the flow channel connecting the respective portions may be disposed in housing 910. Waste liquid container 420A, medium container 440, and cleaning solution container 480 are not necessarily accommodated in housing 910. For example, waste liquid container 420A, medium container 440, and cleaning solution container 480 may be configured separately from housing 910 and accommodating body 920. Waste liquid container 420A, medium container 440, and cleaning solution container 480 may be provided in accommodating body 920.

[Aspects]

It is understood by those skilled in the art that the plurality of embodiments described above are specific examples of the following aspects.

(Item 1) A preprocessing device according to one aspect includes: a sample container that accommodates a liquid sample containing a blood cell; a first filter unit that includes a first filter for removing the blood cell from the liquid sample in the sample container; and a second filter unit that includes a second filter, a first connection unit, and a second connection unit, the second filter configured to capture a microorganism that can be contained in the liquid sample, and the first connection unit and the second connection unit facing each other with the second filter interposed between the first connection unit and the second connection unit. A bubble point of the second filter is higher than a bubble point of the first filter. A first flow channel, a second flow channel, and a third flow channel are formed in the preprocessing device. The first flow channel connects the second filter unit to the sample container and the first filter unit through the first connection unit, and connects the second filter unit to a waste liquid recovery unit that receives a waste liquid discharged from the second filter unit, through the second connection unit. The second flow channel connects the second filter unit to a cleaning solution accommodation unit that accommodates a cleaning solution for cleaning the second filter, through the first connection unit, and connects the second filter unit to the waste liquid recovery unit through the second connection unit. The third flow channel connects the second filter unit to a recovered liquid accommodation unit that accommodates a recovered liquid for recovering the microorganism captured by the second filter, through the second connection unit, and connects the second filter unit to a recovery unit that accommodates the recovered liquid passing through the second filter unit, through the first connection unit. The preprocessing device further includes a blocking element that blocks the first flow channel in response to a decrease in a remaining amount of the liquid sample in an upstream position with respect to the second filter unit in the first flow channel.

The preprocessing device described in item 1 can recover the microorganism filtered by the second filter unit together with the recovery solution by causing the liquid sample to flow from the sample container in the first flow channel to filter the microorganism by the second filter unit, cleaning the second filter of the second filter unit in the second flow channel, and causing the recovery solution to flow toward the second filter unit in the third flow channel. Thus, according to the preprocessing device described in item 1, the microorganism can be separated and recovered from the second filter unit by flowing force of the recovery solution, and the recovery of the microorganism can be automated.

The preprocessing device described in item 1 also removes the blood cell from the liquid sample in the sample container using the first filter, and filters the microorganism from the filtrate of the first filter using the second filter having the bubble point higher than that of the first filter. The preprocessing device described in item 1 further includes the blocking element to block the first flow channel according to the decrease in the remaining amount of the sample container upstream the second filter unit in the first flow channel. Thus, in the first flow channel, a situation in which air is mixed into the second filter unit due to the empty sample container to fill the first connection unit side of the second filter with the air can be avoided.

It is assumed that a composition of the liquid sample is not constant. Thus, viscosity of the liquid sample is not constant and the flow rate of the liquid sample flowing through the first flow channel is not constant, and thus the time from start of supplying the liquid sample from the sample container until the sample container becomes empty is assumed to be different for each preprocessing even if the amount of the liquid sample accommodated in the sample container is constant in each of the plurality of times of preprocessing. In this respect, according to the preprocessing device described in item 1, the first flow channel is blocked according to the decrease in the remaining amount of the liquid sample upstream the second filter unit in the first flow channel. Thus, even when the composition of the liquid sample changes, a situation in which the first connection unit side of the second filter is filled with the air can be reliably avoided.

(Item 2) The blocking element may include: a bubble sensor that detects presence or absence of a bubble upstream the second filter unit in the first flow channel; a switch that switches opening and closing of a predetermined portion upstream the second filter unit of the first flow channel; and a controller that controls the switch to close the predetermined portion in response to the bubble sensor detecting the bubble.

According to the preprocessing device described in item 2, the predetermined portion upstream the second filter unit is closed according to the control of the controller in response to the detection output of the bubble sensor, so that the situation in which the first connection unit side of the second filter is filled with the air can be more reliably avoided.

(Item 3) The preprocessing device described in item 1, the blocking element may include: a sensor that detects the remaining amount of the liquid sample in the sample container; a switch that switches opening and closing of a predetermined portion upstream the second filter unit of the first flow channel; and a controller that causes the switch to close the predetermined portion in response to the sensor detecting that the remaining amount is less than or equal to a predetermined value.

According to the preprocessing device described in item 3, the predetermined portion upstream the second filter unit is closed according to the control of the controller in response to the detection output of the sensor, so that the situation in which the first connection unit side of the second filter is filled with the air can be more reliably avoided.

(Item 4) The preprocessing device described in item 1, the sample container may include an opening through which the liquid sample in the sample container flows into the first flow channel, and the blocking element may include a member in which a state changes so as to close the opening according to a decrease in the remaining amount of the liquid sample in the sample container.

According to the preprocessing device described in item 4, the opening of the sample container is closed by the change in the state of the member, so that the situation in which the first connection unit side of the second filter is filled with the air can be avoided without requiring power consumption of the controller or the like.

(Item 5) In the pretreatment device according to any one of items 1 to 4, the recovered liquid may be a liquid medium used for culturing the microorganism.

According to the preprocessing device described in item 5, after the microorganism filtered by the second filter unit is recovered together with the recovery solution, the recovered solution can be used as it is for culture. In addition, the microorganism is directly recovered in the liquid medium used for culture, so that recovery efficiency of the microorganism can be improved.

(Item 6) A preprocessing method according to another aspect includes removing a removing target from a liquid sample accommodated in a sample container using a first filter and filtering a microorganism from a filtrate of the first filter using a second filter. A bubble point of the second filter is higher than a bubble point of the first filter. The filtering the microorganism includes supplying the filtrate of the first filter to one side of the second filter and receiving a waste liquid from another side of the second filter. The preprocessing method of the another aspect further includes: blocking a flow channel between the second filter unit and the sample container in response to a decrease in a remaining amount of the liquid sample in an upstream position with respect to the second filter unit in the filtering the microorganism; supplying a cleaning solution to the one side of the second filter and receiving a waste liquid from the other side of the second filter to clean the second filter; and supplying a recovered liquid to the other side of the second filter and receiving the recovered liquid from the one side of the second filter to recover the microorganism from the second filter.

The preprocessing method described in item 6 can recover the microorganism filtered by the second filter together with the recovery solution by causing the liquid sample to flow from the sample container in the first flow channel to filter the microorganism by the second filter, cleaning the second filter in the second flow channel, and causing the recovery solution to flow toward the second filter in the third flow channel. Thus, according to the preprocessing method described in item 6, the microorganism can be separated and recovered from the second filter by flowing force of the recovery solution, and the recovery of the microorganism can be automated.

The preprocessing method described in item 6 also removes the removing target from the liquid sample in the sample container using the first filter, and filters the microorganism from the filtrate of the first filter using the second filter having the bubble point higher than that of the first filter. In the preprocessing method described in item 6, the first flow channel is blocked according to the decrease in the remaining amount of the sample container upstream the second filter in the first flow channel. Thus, in the first flow channel, the situation in which air is mixed into the second filter due to the empty sample container to fill one side of the second filter with the air can be avoided.

It is assumed that a composition of the liquid sample is not constant. Thus, viscosity of the liquid sample is not constant and the flow rate of the liquid sample flowing through the first flow channel is not constant, and thus the time from start of supplying the liquid sample from the sample container until the sample container becomes empty is assumed to be different for each preprocessing even if the amount of the liquid sample accommodated in the sample container is constant in each of the plurality of times of preprocessing. In this respect, according to the preprocessing method described in item 6, the first flow channel is blocked according to the decrease in the remaining amount of the liquid sample upstream the second filter in the first flow channel. Thus, even when the composition of the liquid sample changes, the situation in which one side of the second filter is filled with the air can be reliably avoided.

(Item 7) A non-transitory computer-readable medium storing a program executed by a computer to control a preprocessing device including a first filter and a second filter, the program may cause the computer to remove a removing target from a liquid sample accommodated in a sample container using the first filter and filter a microorganism from a filtrate of the first filter using the second filter. A bubble point of the second filter may be higher than a bubble point of the first filter. The filtering the microorganism may include supplying the filtrate of the first filter to one side of the second filter and receive a waste liquid from an other side of the second filter. The program further causes the computer to: block a flow channel between the second filter unit and the sample container in response to a decrease in a remaining amount of the liquid sample in an upstream position with respect to the second filter unit in the filtering the microorganism; supply a cleaning solution to the one side of the second filter and receive a waste liquid from the other side of the second filter to clean the second filter; and supply a recovered liquid to the other side of the second filter and receive the recovered liquid from the one side of the second filter to recover the microorganism from the second filter.

The program described in item 7 causes the computer to cause the liquid sample to flow from the sample container in the first flow channel to filter the microorganism using the second filter, then cause the second filter to be cleaned in the second flow channel, and further cause the recovery solution to flow toward the second filter in the third flow channel to recover the microorganism filtered by the second filter together with the recovery solution. Thus, according to the program described in item 7, the microorganism can be separated and recovered from the second filter by flowing force of the recovery solution, and the recovery of the microorganism can be automated.

The program described in item 7 also causes the computer to remove a removing target from the liquid sample in the sample container using the first filter, and filter the microorganism from the filtrate of the first filter using the second filter having the bubble point higher than that of the first filter. The program described in item 7 further causes the computer to block the first flow channel when the remaining amount of the sample container upstream the second filter of the first flow channel falls below a predetermined value. Thus, in the first flow channel, the situation in which air is mixed into the second filter due to the empty sample container to fill one side of the second filter with the air can be avoided.

It is assumed that a composition of the liquid sample is not constant. Thus, viscosity of the liquid sample is not constant and the flow rate of the liquid sample flowing through the first flow channel is not constant, and thus the time from start of supplying the liquid sample from the sample container until the sample container becomes empty is assumed to be different for each preprocessing even if the amount of the liquid sample accommodated in the sample container is constant in each of the plurality of times of preprocessing. In this respect, according to the program described in item 7, the computer blocks the first flow channel according to the decrease in the remaining amount of the liquid sample on the upstream side of the second filter of the first flow channel. Thus, even when the composition of the liquid sample changes, the situation in which one side of the second filter is filled with the air can be reliably avoided.

Although the embodiments of the present invention have been described, it should be considered that the disclosed embodiments are an example in all respects and not restrictive. The scope of the present invention is indicated by the claims, and it is intended that all modifications within the meaning and scope of the claims are included in the present invention.

What is claimed is:

1. A preprocessing device for a liquid sample, the preprocessing device comprising:
   a sample container that accommodates a liquid sample containing a blood cell;
   a first filter unit that includes a first filter for removing the blood cell from the liquid sample in the sample container;
   a second filter unit that includes a second filter, a first connection unit, and a second connection unit, the second filter configured to capture a microorganism that can be contained in the liquid sample, the first connection unit and the second connection unit facing each other with the second filter interposed therebetween, and a bubble point of the second filter being higher than a bubble point of the first filter;
   a first flow channel, a second flow channel, and a third flow channel being formed in the preprocessing device,
   the first flow channel connecting the second filter unit to the sample container and the first filter unit through the first connection unit,
   the first flow channel connecting the second filter unit to a waste liquid recovery unit that receives a waste liquid discharged from the second filter unit, through the second connection unit,
   the second flow channel connecting the second filter unit to a cleaning solution accommodation unit that accommodates a cleaning solution for cleaning the second filter, through the first connection unit,
   the second flow channel connecting the second filter unit to the waste liquid recovery unit through the second connection unit,
   the third flow channel connecting the second filter unit to a recovered liquid accommodation unit that accommodates a recovered liquid for recovering the microorganism captured by the second filter, through the second connection unit, and
   the third flow channel connecting the second filter unit to a recovery unit that accommodates the recovered liquid passing through the second filter unit, through the first connection unit; and
   a blocking element configured to block the first flow channel in response to a decrease in a remaining amount of the liquid sample in an upstream position with respect to the second filter unit in the first flow channel.

2. The preprocessing device according to claim 1, wherein the blocking element includes:
   a bubble sensor that detects presence or absence of a bubble upstream the second filter unit in the first flow channel;
   a switch that switches opening and closing of a predetermined portion upstream the second filter unit of the first flow channel; and
   a controller that controls the switch to close the predetermined portion in response to the bubble sensor detecting the bubble.

3. The preprocessing device according to claim 1, wherein the blocking element includes:
   a sensor that detects the remaining amount of the liquid sample in the sample container;
   a switch that switches opening and closing of a predetermined portion upstream the second filter unit of the first flow channel; and
   a controller that causes the switch to close the predetermined portion in response to the sensor detecting that the remaining amount is less than or equal to a predetermined value.

4. The preprocessing device according to claim 1, wherein
the sample container includes an opening through which the liquid sample in the sample container flows into the first flow channel, and
the blocking element includes a member in which a state changes so as to close the opening according to a decrease in the remaining amount of the liquid sample in the sample container.

5. The preprocessing device according to claim 1, wherein the recovered liquid is a liquid medium used for culturing the microorganism.

6. A preprocessing method comprising:
removing a removing target from a liquid sample accommodated in a sample container using a first filter and filtering a microorganism from a filtrate of the first filter using a second filter, a bubble point of the second filter being higher than a bubble point of the first filter, the filtering the microorganism including supplying the filtrate of the first filter to one side of the second filter and receiving a waste liquid from another side of the second filter;
blocking a flow channel between the second filter and the sample container in response to a decrease in a remaining amount of the liquid sample in an upstream position with respect to the second filter in the filtering the microorganism;
supplying a cleaning solution to the one side of the second filter and receiving a waste liquid from the other side of the second filter to clean the second filter; and
supplying a recovered liquid to the other side of the second filter and receiving the recovered liquid from the one side of the second filter to recover the microorganism from the second filter.

7. A non-transitory computer-readable medium storing a program executed by a computer to control a preprocessing device including a first filter and a second filter, wherein the computer is programmed to:
remove a removing target from a liquid sample accommodated in a sample container using the first filter and filter a microorganism from a filtrate of the first filter using the second filter, a bubble point of the second filter being higher than a bubble point of the first filter, the filtering the microorganism including supplying the filtrate of the first filter to one side of the second filter and receiving a waste liquid from an other side of the second filter;
block a flow channel between the second filter and the sample container in response to a decrease in a remaining amount of the liquid sample in an upstream position with respect to the second filter in the filtering the microorganism;
supply a cleaning solution to the one side of the second filter and receive a waste liquid from the other side of the second filter to clean the second filter; and
supply a recovered liquid to the other side of the second filter and receive the recovered liquid from the one side of the second filter to recover the microorganism from the second filter.

* * * * *